(12) United States Patent
Trese et al.

(10) Patent No.: US 10,202,429 B2
(45) Date of Patent: Feb. 12, 2019

(54) NORRIN REGULATION OF CELLULAR PRODUCTION OF JUNCTION PROTEINS AND USE TO TREAT RETINAL VASCULATURE EDEMA

(71) Applicant: RETINAL SOLUTIONS LLC, Ann Arbor, MI (US)

(72) Inventors: Michael T. Trese, Novi, MI (US); Antonio Capone, Jr., Novi, MI (US); Kimberly Drenser, Novi, MI (US)

(73) Assignee: RETINAL SOLUTIONS LLC, Ann Arbor, MI (US)

( * ) Notice: Subject to any disclaimer, the term of this patent is extended or adjusted under 35 U.S.C. 154(b) by 0 days.

(21) Appl. No.: 14/733,729

(22) Filed: Jun. 8, 2015

(65) Prior Publication Data
US 2016/0355559 A1   Dec. 8, 2016

(51) Int. Cl.
| | |
|---|---|
| *A61K 38/18* | (2006.01) |
| *A61P 27/02* | (2006.01) |
| *C07K 14/47* | (2006.01) |
| *A61K 38/17* | (2006.01) |
| *C07K 14/475* | (2006.01) |
| *C07K 14/515* | (2006.01) |
| *A61K 38/00* | (2006.01) |

(52) U.S. Cl.
CPC ...... *C07K 14/4705* (2013.01); *A61K 38/1709* (2013.01); *A61K 38/1891* (2013.01); *A61P 27/02* (2018.01); *A61K 38/00* (2013.01); *C07K 14/475* (2013.01); *C07K 14/515* (2013.01)

(58) Field of Classification Search
CPC .................................................. C07K 14/4705
See application file for complete search history.

(56) References Cited

U.S. PATENT DOCUMENTS

| | | | |
|---|---|---|---|
| 4,588,585 A | 5/1986 | Mark et al. | |
| 5,378,475 A | 1/1995 | Smith et al. | |
| 5,773,019 A | 6/1998 | Ashton et al. | |
| 6,001,386 A | 12/1999 | Ashton et al. | |
| 6,217,895 B1 | 4/2001 | Guo et al. | |
| 6,375,972 B1 | 4/2002 | Guo et al. | |
| 6,756,058 B2 | 6/2004 | Brubaker et al. | |
| 9,114,078 B2 * | 8/2015 | Drenser | A61K 9/0019 |
| 2004/0054374 A1 | 3/2004 | Weber et al. | |
| 2005/0281861 A1 | 12/2005 | Hughes et al. | |
| 2010/0129375 A1 | 5/2010 | Junge et al. | |
| 2010/0239499 A1 * | 9/2010 | Drenser | A61K 9/0019 424/9.2 |

FOREIGN PATENT DOCUMENTS

| | | |
|---|---|---|
| WO | 2009114878 A2 | 9/2009 |
| WO | 2014143022 A1 | 9/2014 |

OTHER PUBLICATIONS

Chen et al., Stroke. Feb. 2015.45(2):529-536. Epub Dec. 30, 2014 (attached as pp. 1-11).*
Chen et al., Stroke. Apr. 2015 46(4)e91. Epub Feb. 26, 2015 (attached as pp. 1-2).*
Braunger et al., Neurobiology of Disease. 2013. 50:1-12.*
Ke et al., Genes and Dev. 2013. 27:2305-2319.*
Lee et al., Acta Histochemica. 2013. 115:447-451.*
Ohlmann et al., Prog Retinal Eye Res. 2012. 31:243-257.ePub Feb. 21, 2012.*
Paes et al., Invest. Opthamol Visual Sci. Aug 2011.52(9):6452-6461.*
Ye et al., Cell. Oct. 16, 2009;139(2):285-298.*
Zhou et al., J Clin Invest. Sep. 2014.124(9):3825-3846.*
Taddei et al., (Nature Cell Bio. Aug. 2008;10(8)923-934 and attached Supplementary Information pp. 1-15).*
Groten et al., (Human Reprod. 2006;21(12):3096-3102).*
National Eye Institute definition of Macular Edema at www.nei.nih.gov/faqs/retina-macular-edema (Apr. 5, 2010); last accessed Sep. 7, 2017.*
Weidemann et al., (Clin Cosmet Investig Dermatol. 2013; 6: 233-244. Published online Sep. 26, 2013).*
Daily, Wendy; Roumayah, Kevin; Cheng, Mei; Massol, Charlote; Drenser, Kimberly A.; Mitton, Kenneth P.; Trese, Michael Thomas, "Norrin Increases Vessel Integrity upon VEGF Induced Permeability" from IOVS-ARVO-Journals; Apr. 2014, vol. 55, Issue 13, //iovs.arvojournals.org/article.aspx?articleid=2271009.
Wang, Yanshu; Rattner, Amir; Zhou, Yulian; Williams, John; Smallwood, Philip M.; Nathans, Jeremy, "Norrin/Frizzled4 Signaling in Retinal Vascular Development and Blood Brain Barrier Plasticity", 13 pp; 1332 Cell 151, 1332-1344, Dec. 7, 2012 ª2012 Elsevier Inc.
Taddei, Andrea et al., "Endothelial adherens junctions control tight junctions by VE-cadherin-mediated upregulation of claudin-5", Nature Cell Biology, Aug. 2008, pp. 923-934, vol. 10, issue 8, Macmillan Publishers Limited (2008).
Gavard, Julie and Gutkind, J. Silvio, "VEGF controls endothelial-cell permeability by promoting the β-arrestin-dependent endocytosis of VE-cadherin", Nature Cell Biology, Nov. 2006, pp. 1223-1234, vol. 8, issue 11, Nature Publishing Group (2006).
Xu, Qiang et al., "Vascular Development in the Retina and Inner Ear: Control by Norrin and Frizzled-4, a High-Affinity Ligand-Receptor Pair", Cell, Mar. 19, 2004, pp. 883-895, vol. 116, Cell Press (2004).
Clevers, Hans, "Wnt Signaling: Ig-Norrin the Dogma", Current Biology, Jun. 8, 2004, pp. R436-R437, vol. 14, Elsevier Ltd. (2004).
Niehrs, Christof, "Norrin and Frizzled: A New Vein for the Eye", Developmental Cell, Apr. 2004, pp. 453-461, vol. 6, Cell Press (2004).
Willert, Karl and Nusse, Roel, "β-catenin: a key mediator of Wnt signaling", Current Opinion in Genetics & Development, 1998, pp. 95-102, vol. 8, Current Biology Ltd (1998).

(Continued)

*Primary Examiner* — Zachary C Howard
(74) *Attorney, Agent, or Firm* — Avery N. Goldstein; Blue Filament Law PLLC

(57) ABSTRACT

A method of tightening inter-cellular junctions in retinal or choroidal vessel cells includes exposing the retinal or choroidal vessel cells to norrin. Upon sufficient contact time, for norrin to selectively up-regulate gene expression of VE-cadherin or claudin-5 in the retinal or choroidal vessel cells, the inter-cellular junctions are tightened. The method is also suitable for treating retinal pigment epithelial cells in wet macular degeneration.

13 Claims, 5 Drawing Sheets

Specification includes a Sequence Listing.

(56) References Cited

OTHER PUBLICATIONS

Meitinger, Thomas et al., "Molecular Modeling of the Norrie Disease Protein Predicts a Cystine Knot Growth Factor Tertiary Structure", Nature Genetics, Dec. 1993, pp. 376-380, vol. 5.

Berger, Wolfgang et al., "An animal model for Norrie disease (ND): gene targeting of the mouse ND gene", Human Molecular Genetics, 1996, pp. 51-59, vol. 5, issue 1, Oxford University Press (1996).

Smallwood, Philip M. et al., "Mutational Analysis of Norrin-Frizzled4 Recognition", The Journal of Biological Chemistry, Feb. 9, 2007, pp. 4057-4068, vol. 282, issue 6, The American Society for Biochemistry and Molecular Biology, Inc. (2007), U.S.A.

Ke, Jiyuan et al., "Structure and function of Norrin in assembly and activation of a Frizzled 4-Lrp5/6 complex", Genes and Development, 2013, pp. 2305-2319, vol. 27, Cold Spring Harbor Laboratory Press.

Mark, D.F., Lu, S.D., Creasey, A.A., Yamamoto, R., and Lin, L.S., "Site-specific mutagenesis of the human fibroblast interferon gene", Proceedings of the National Academy of Sciences, Sep. 1984, pp. 5662-5666, vol. 81.

Jiang, Caihui et al., "Intravitreal injections of GDNF-loaded biodegradable microspheres are neuroprotective in a rat model of glaucoma", Molecular Vision, Sep. 24, 2007, pp. 1783-1792, vol. 13, Molecular Vision (2007).

Fu, Karen et al., "A Potential Approach for Decreasing the Burst Effect of Protein from PLGA Microspheres", Journal of Pharmaceutical Sciences, Aug. 2003, pp. 1582-1591, vol. 92, issue 8.

\* cited by examiner

PRIOR ART FIG. 1

SEQUENCE LISTING

```
<160> NUMBER OF SEQ ID NOS: 21

<210> SEQ ID NO 1
<211> LENGTH: 133
<212> TYPE: PRT
<213> ORGANISM: Homo sapiens

<400> SEQUENCE: 1

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130

<210> SEQ ID NO 2
<211> LENGTH: 109
<212> TYPE: PRT
<213> ORGANISM: Artificial sequence
<220> FEATURE:
<223> OTHER INFORMATION: Synthetic

<400> SEQUENCE: 2

Lys Thr Asp Ser Ser Phe Ile Met Asp Ser Asp Pro Arg Arg Cys Met
1               5                   10                  15

Arg His His Tyr Val Asp Ser Ile Ser His Pro Leu Tyr Lys Cys Ser
            20                  25                  30

Ser Lys Met Val Leu Leu Ala Arg Cys Glu Gly His Cys Ser Gln Ala
        35                  40                  45
```

```
Ser Arg Ser Glu Pro Leu Val Ser Phe Ser Thr Val Leu Lys Gln Pro
 50                  55                  60

Phe Arg Ser Ser Cys His Cys Arg Pro Gln Thr Ser Lys Leu Lys
 65                  70                  75                  80

Ala Leu Arg Leu Arg Cys Ser Gly Gly Met Arg Leu Thr Ala Thr Tyr
                 85                  90                  95

Arg Tyr Ile Leu Ser Cys His Cys Glu Glu Cys Asn Ser
            100                 105
```

<210> SEQ ID NO 3
<211> LENGTH: 133
<212> TYPE: PRT
<213> ORGANISM: Artificial sequence
<220> FEATURE:
<223> OTHER INFORMATION: Synthetic

<400> SEQUENCE: 3

```
Met Arg Lys His Val Leu Ala Ala Ser Phe Ser Met Leu Ser Leu Leu
 1               5                  10                  15

Val Ile Met Gly Asp Thr Asp Ser Lys Thr Asp Ser Ser Phe Ile Met
                 20                  25                  30

Asp Ser Asp Pro Arg Arg Cys Met Arg His His Tyr Val Asp Ser Ile
             35                  40                  45

Ser His Pro Leu Tyr Lys Cys Ser Ser Lys Met Val Leu Leu Ala Glu
 50                  55                  60

Cys Glu Gly His Cys Ser Gln Ala Ser Arg Ser Glu Pro Leu Val Ser
 65                  70                  75                  80

Phe Ser Thr Val Leu Lys Gln Pro Phe Arg Ser Ser Cys His Cys Cys
                 85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
            115                 120                 125

Glu Glu Cys Asn Ser
        130
```

<210> SEQ ID NO 4
<211> LENGTH: 133
<212> TYPE: PRT
<213> ORGANISM: Artificial sequence
<220> FEATURE:
<223> OTHER INFORMATION: Synthethic

<400> SEQUENCE: 4

```
Met Arg Lys His Val Leu Ala Ala Ser Phe Ser Met Leu Ser Leu Leu
 1               5                  10                  15

Val Ile Met Gly Asp Thr Asp Ser Lys Ala Asp Ser Ser Phe Ile Met
                 20                  25                  30

Asp Ser Asp Pro Arg Arg Cys Met Arg His His Tyr Val Asp Ser Ile
             35                  40                  45

Ser His Pro Leu Tyr Lys Cys Ser Ser Lys Met Val Leu Leu Ala Arg
 50                  55                  60

Cys Glu Gly His Cys Ser Gln Ala Ser Arg Ser Glu Pro Leu Val Ser
 65                  70                  75                  80

Phe Ser Thr Val Leu Lys Gln Pro Phe Arg Ser Ser Cys His Cys Cys
                 85                  90                  95

Arg Pro Gln Thr Ser Lys Leu Lys Ala Leu Arg Leu Arg Cys Ser Gly
            100                 105                 110
```

Gly Met Arg Leu Thr Ala Thr Tyr Arg Tyr Ile Leu Ser Cys His Cys
            115                 120                 125

Glu Glu Cys Asn Ser
        130

<210> SEQ ID NO 5
<211> LENGTH: 133
<212> TYPE: PRT
<213> ORGANISM: Artificial sequence
<220> FEATURE:
<223> OTHER INFORMATION: Synthetic

<400> SEQUENCE: 5

Met Arg Lys His Val Leu Ala Ala Ser Phe Ser Met Leu Ser Leu Leu
1               5                   10                  15

Val Ile Met Gly Asp Thr Asp Ser Lys Thr Asp Ala Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
            115                 120                 125

Glu Glu Cys Asn Ser
        130

<210> SEQ ID NO 6
<211> LENGTH: 133
<212> TYPE: PRT
<213> ORGANISM: Artificial sequence
<220> FEATURE:
<223> OTHER INFORMATION: Synthetic

<400> SEQUENCE: 6

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ala Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
            115                 120                 125

Glu Glu Cys Asn Ser
        130

```
<210> SEQ ID NO 7
<211> LENGTH: 133
<212> TYPE: PRT
<213> ORGANISM: Artificial sequence
<220> FEATURE:
<223> OTHER INFORMATION: Synthetic

<400> SEQUENCE: 7
```

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Ala Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130

```
<210> SEQ ID NO 8
<211> LENGTH: 133
<212> TYPE: PRT
<213> ORGANISM: Artificial sequence
<220> FEATURE:
<223> OTHER INFORMATION: Synthetic

<400> SEQUENCE: 8
```

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Ala Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130

```
<210> SEQ ID NO 9
<211> LENGTH: 133
<212> TYPE: PRT
<213> ORGANISM: Artificial sequence
```

<220> FEATURE:
<223> OTHER INFORMATION: Synthetic

<400> SEQUENCE: 9

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Ala Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
            115                 120                 125

Glu Glu Cys Asn Ser
        130

<210> SEQ ID NO 10
<211> LENGTH: 133
<212> TYPE: PRT
<213> ORGANISM: Artificial sequence
<220> FEATURE:
<223> OTHER INFORMATION: Synthetic

<400> SEQUENCE: 10

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Ala Arg Tyr Ile Leu Ser Cys His Cys
            115                 120                 125

Glu Glu Cys Asn Ser
        130

<210> SEQ ID NO 11
<211> LENGTH: 133
<212> TYPE: PRT
<213> ORGANISM: Artificial sequence
<220> FEATURE:
<223> OTHER INFORMATION: Synthetic

<400> SEQUENCE: 11

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
                20                  25                  30

Asp Ser Asp Pro Arg Arg Cys Met Arg His His Tyr Val Asp Ser Ile
            35                  40                  45

Ser His Pro Leu Tyr Lys Cys Ser Ser Lys Met Val Leu Leu Ala Arg
        50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
                100                 105                 110

Gly Met Arg Leu Thr Ala Thr Tyr Ala Tyr Ile Leu Ser Cys His Cys
            115                 120                 125

Glu Glu Cys Asn Ser
        130

<210> SEQ ID NO 12
<211> LENGTH: 133
<212> TYPE: PRT
<213> ORGANISM: Artificial sequence
<220> FEATURE:
<223> OTHER INFORMATION: Synthetic

<400> SEQUENCE: 12

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
                20                  25                  30

Asp Ser Asp Pro Arg Arg Cys Met Arg His His Tyr Val Asp Ser Ile
            35                  40                  45

Ser His Pro Leu Tyr Lys Cys Ser Ser Lys Met Val Leu Leu Ala Arg
        50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
                100                 105                 110

Gly Met Arg Leu Thr Ala Thr Tyr Arg Ala Ile Leu Ser Cys His Cys
            115                 120                 125

Glu Glu Cys Asn Ser
        130

<210> SEQ ID NO 13
<211> LENGTH: 133
<212> TYPE: PRT
<213> ORGANISM: Artificial sequence
<220> FEATURE:
<223> OTHER INFORMATION: Synthetic

<400> SEQUENCE: 13

```
Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys Ala Cys
        115                 120                 125

Glu Glu Cys Asn Ser
        130
```

<210> SEQ ID NO 14
<211> LENGTH: 133
<212> TYPE: PRT
<213> ORGANISM: Artificial sequence
<220> FEATURE:
<223> OTHER INFORMATION: Synthetic

<400> SEQUENCE: 14

```
Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Ala Glu Cys Asn Ser
        130
```

<210> SEQ ID NO 15
<211> LENGTH: 133
<212> TYPE: PRT
<213> ORGANISM: Artificial sequence
<220> FEATURE:
<223> OTHER INFORMATION: Synthetic

<400> SEQUENCE: 15

```
Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Ala Cys Asn Ser
        130
```

<210> SEQ ID NO 16
<211> LENGTH: 133
<212> TYPE: PRT
<213> ORGANISM: Artificial sequence
<220> FEATURE:
<223> OTHER INFORMATION: Synthetic

<400> SEQUENCE: 16

```
Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Glu Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
        130
```

<210> SEQ ID NO 17
<211> LENGTH: 133
<212> TYPE: PRT
<213> ORGANISM: Artificial sequence
<220> FEATURE:
<223> OTHER INFORMATION: Synthetic

<400> SEQUENCE: 17

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Glu Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
        130

<210> SEQ ID NO 18
<211> LENGTH: 133
<212> TYPE: PRT
<213> ORGANISM: Artificial sequence
<220> FEATURE:
<223> OTHER INFORMATION: Synthetic

<400> SEQUENCE: 18

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Glu Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
        130

<210> SEQ ID NO 19
<211> LENGTH: 133
<212> TYPE: PRT
<213> ORGANISM: Artificial sequence
<220> FEATURE:
<223> OTHER INFORMATION: Synthetic

<400> SEQUENCE: 19

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Glu Leu Lys Ala Leu Arg Leu Arg Cys Ser Gly
            100                 105                 110

Gly Met Arg Leu Thr Ala Thr Tyr Arg Tyr Ile Leu Ser Cys His Cys
            115                 120                 125

Glu Glu Cys Asn Ser
        130

<210> SEQ ID NO 20
<211> LENGTH: 133
<212> TYPE: PRT
<213> ORGANISM: Artificial sequence
<220> FEATURE:
<223> OTHER INFORMATION: Synthetic

<400> SEQUENCE: 20

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Glu Ala Leu Arg Leu Arg Cys Ser Gly
            100                 105                 110

Gly Met Arg Leu Thr Ala Thr Tyr Arg Tyr Ile Leu Ser Cys His Cys
            115                 120                 125

Glu Glu Cys Asn Ser
        130

<210> SEQ ID NO 21
<211> LENGTH: 133
<212> TYPE: PRT
<213> ORGANISM: Artificial sequence
<220> FEATURE:
<223> OTHER INFORMATION: Synthetic

```
<400> SEQUENCE: 21

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
                20                  25                  30

Asp Ser Asp Pro Arg Arg Cys Met Arg His His Tyr Val Asp Ser Ile
            35                  40                  45

Ser His Pro Leu Tyr Lys Cys Ser Ser Lys Met Val Leu Leu Ala Arg
        50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
                100                 105                 110

Gly Met Glu Leu Thr Ala Thr Tyr Arg Tyr Ile Leu Ser Cys His Cys
            115                 120                 125

Glu Glu Cys Asn Ser
            130
```

NORRIN REGULATION OF CELLULAR PRODUCTION OF JUNCTION PROTEINS AND USE TO TREAT RETINAL VASCULATURE EDEMA

FIELD OF THE INVENTION

The present invention is directed generally to methods of regulating VE-cadherin and claudin gene expression in retinal tissue by applying to such tissue norrin protein; and in particular, to produce additional cellular production of VE-cadherin and claudin-5 in retinal vasculature to limit edema associated with compromised retinal vasculature Tight Junctions.

BACKGROUND OF THE INVENTION

Various retinopathies cause regions of leakage induced edema within the retina. To compensate for the lack of oxygen & nutrients in the ischemic tissue, cytokines involved in permeability are excessively up-regulated. The over-expression of vascular endothelial growth factor (VEGF) causes an increase in vessel permeability due to depletion of cell-to-cell adhesion molecules such as VE-cadherin and claudin-5.

The increased permeability of vasculature in the eye can result in edema. While clinical characterization of the causes of edema such as diabetes have been studied, little attention has been paid to addressing the weakened inter-cellular junctions in retinal vasculature. The edema associated with vasculature leakage can cause complications such as macular edema and exudative retinal detachment.

The epithelium including retinal pigment epithelium function to separate blood in the circulatory system from other tissues. The epithelium are sites of exchange as well as barriers, for the transit of ions and molecules between tissues and the circulatory system of the organism. Complexes between adjacent cells include Tight Junctions and Adherens junctions. Vertebrate epithelial cells exhibit Tight Junctions that lie apical to Adherens Junctions. Tight junctions have an organizing role in epithelial polarization and establish an apico-lateral barrier to the diffusion of solutes through the intracellular space (gate function). Tight junctions also restrict the movement of lipids and membrane proteins between the apical and the basolateral membrane (fence function). Tight Junctions are highly ordered membrane contact sites, comprising a network of intra-membrane fibrils. Tight Junctions include transmembrane proteins, including occludin, claudin-5, and junctional adhesion molecules (JAMs), and a number of cytoplasmic peripheral proteins. These are shown schematically in prior art FIG. 1. While the transmembrane proteins mediate cell-cell adhesion, the cytosolic tight junction plaque contains various types of proteins (e.g. PDZ proteins, such as the ZO (Zona Occludens) family) that link tight junction transmembrane proteins to the underlying cytoskeleton. These adapters also recruit regulatory proteins, such as protein kinases, phosphatases, small GTPases and transcription factors, to the tight junctions. As a result, structural (Actin and Spectrin) and regulatory (Actin-binding proteins, GTPases and kinases) proteins are juxtaposed with transmembrane proteins. This protein scaffolding facilitates the assembly of highly ordered structures, such as junctional complexes or signaling patches that regulate epithelial cell polarity, proliferation and differentiation. This scaffolding is also operative in retinal pigment epithelium.

Tight Junctions are located at the uppermost portion of the lateral plasma membrane, where the integral membrane proteins like claudins appear to be involved in the homophilic and/or heterophilic interactions implicated in firm adhesions. Claudins have four hydrophobic transmembrane domains and two extracellular loops (the first loop is larger than the second). The extracellular loops, whose sequences are distinct in different claudins, contribute to the formation not only of tight junction strands but also of ion-selective channels. Claudin-5 is important in endothethial and epithelial cell junctions. In general, tight junction strands are linear co-polymers of occludin, claudin-5, and JAMs that attract cytoplasmic proteins containing PDZ domains (OZ) have high affinity for the C-terminal sequences of these proteins.

Tight Junctions and Adherens Junctions are functionally and structurally linked, endothelial VE-cadherin associated with Adherens Junctions upregulates the gene encoding the Tight Junction adhesive protein claudin-5. This effect requires the release of the inhibitory activity of forkhead box factor FoxO1 to suppress proteasome activity. Vascular endothelial (VE)-cadherin acts by inducing the phosphorylation of FoxO1 through Akt activation and by limiting the translocation of beta-catenin to the nucleus. (Taddei et al. *Nat Cell Biol.* 2008 August; 10(8):923-34. doi: 10.1038/ncb1752. Epub 2008 Jul. 6). Polycystin-1 (PDK-1) is a membrane protein localized to Adherens Junctions in a complex containing beta-catenins, that is mediated by P13K.

VEGF induces vascular permeability through induction of the rapid endocytosis of a key endothelial cell adhesion molecule, VE-cadherin, thereby disrupting the endothelial barrier function. This process is initiated by the activation of the small GTPase, Rac by VEGFR through the Src-dependent phosphorylation of Vav2 (not shown), a guanine nucleotide-exchange factor. Rac activation, in turn, promotes the p21-activated kinase (PAK)-mediated phosphorylation of a highly conserved motif within the intracellular tail of VE-cadherin. This results in the disassembly of intercellular junctions. (Gavard et al., *Nat Cell Biol.* 2006 November; 8(11):1223-34. Epub 2006 Oct. 22).

In a normally functioning retinal pigment epithelial cell shown in the left panel of FIG. 1 with an intact Tight Junction, VEGF is not bound to its corresponding receptor VEGFR, and claudin-5 is expressed normally in the nucleus from the encoding claudin-5 gene and processed by the endoplasmic reticulum. The occuludin, claudin-5, and and JAM together form a functioning Tight Junction, and VE-cadherin forms and organized Adherens Junction.

In contrast, with VEGF binding to VEGFR, as shown in the right panel of FIG. 1, the Src/Rac/Pak complex acts on beta-catenins to destabilize the Adherens Junction. The resultant cascade is believed to disrupt claudin-5 expression and assembly resulting in a loss of Tight Junction structure.

Norrin is a ligand for the Frizzled receptor subtype 4 (Fz4). Norrin binds Fz4 with nanomolar affinity (Xu, et al, *Cell,* 2004; 116:883-895; Clevers, *Curr Biol,* 2004; 14:R436-437; Nichrs, *Dev Cell,* 2004; 6:453-454). Norrin interaction with Fz4 is dependent on the cell surface receptor LRP5. (Xu, 2004). Frizzled receptors are coupled to the β-catenin canonical signaling pathway. The inactivation of glycogen synthase kinase (GSK) 3β and Axin through frizzled receptor binding stabilizes β-catenin, which subsequently accumulates in the cell nucleus and activates the transduction of target genes that are crucial in the G1-S-phase transition, such as cyclin D1 or c-Myc. (Willert et al., *Curr Opin Genet Dev,* 1998; 8:95-102). Suppression of norrin activity has been shown to preclude angiogenesis associated with ocular disease (US 2010/0129375). Norrin protein has not been implicated in the treatment of edema associated with leaking vasculature in the eye.

Thus, there exists a need for a method to treat retinal edema associated with vasculature leakage. There further exists a need for a method to treat clinical disorders associated with retinal edema. There also exists a need to treat fluid pockets in macular degeneration, as well as FEVR. There also exists a need for a method to produce VE-adherens and claudin-5. The present invention is directed to these, as well as other, important needs in the art.

SUMMARY OF THE INVENTION

A method of tightening inter-cellular junctions in retinal or choroidal vessel cells includes exposing the retinal or choroidal vessel cells to norrin. Upon sufficient contact time, for norrin to selectively up-regulate gene expression of VE-cadherin or claudin-5 in the retinal or choroidal vessel cells, the inter-cellular junctions are tightened. The method is effective in vivo in a human subject. Norrin is readily administered byintraocular injection, administration or topical administration.

A norrin truncate or fragment that is capable of binding a frizzled-4 receptor of a target cell can be used and afford greater solubility than native norrin. The norrin used herein can be recombinant.

A combination composition is provided of an anti-VEGF agent and a norrin.

BRIEF DESCRIPTION OF THE DRAWINGS

These and other aspects of the present invention will be elucidated in the accompanying drawings and following detailed description of the invention.

DETAILED DESCRIPTION OF THE INVENTION

The present invention has utility as a method to make limit inter-cellular leakage between cells in retinal or choroidal vasculature. As a result, an ocular disorder in which ocular or choroidal edema occurs based on leakage of the Adherens Junctions or Tight Junctions is readily treated. The present invention is particularly well-suited for usage in response to the blood-retinal barrier (BRB) compromise. A method is also provided for the production of VE-cadherin and claudin-5. In a particular application, fluid collection under retinal pigment epithelial cells in wet macular degeneration is reduced; a condition currently without effective clinical treatments. The invention will be described in detail below. Those skilled in the art will appreciate that the description given herein is for exemplary purposes only and is not intended in any way to limit the scope of the invention.

Figure 1:
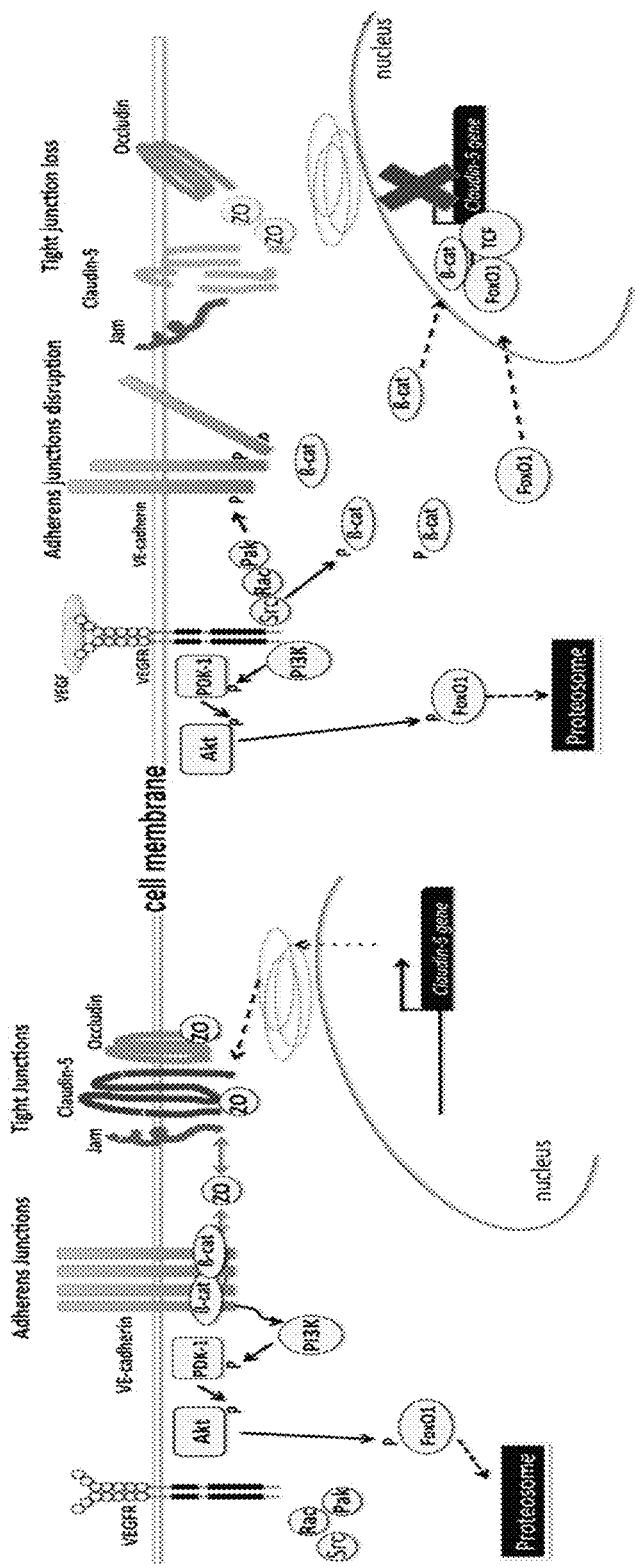
FIG. 1 are prior art schematics of a cell having intact cell junctions (left panel) and weakened or disrupted cell junctions (right panel), showing the function of VEGF in changing the pathway of certain highlighted cellular pathways.
Figure 2:
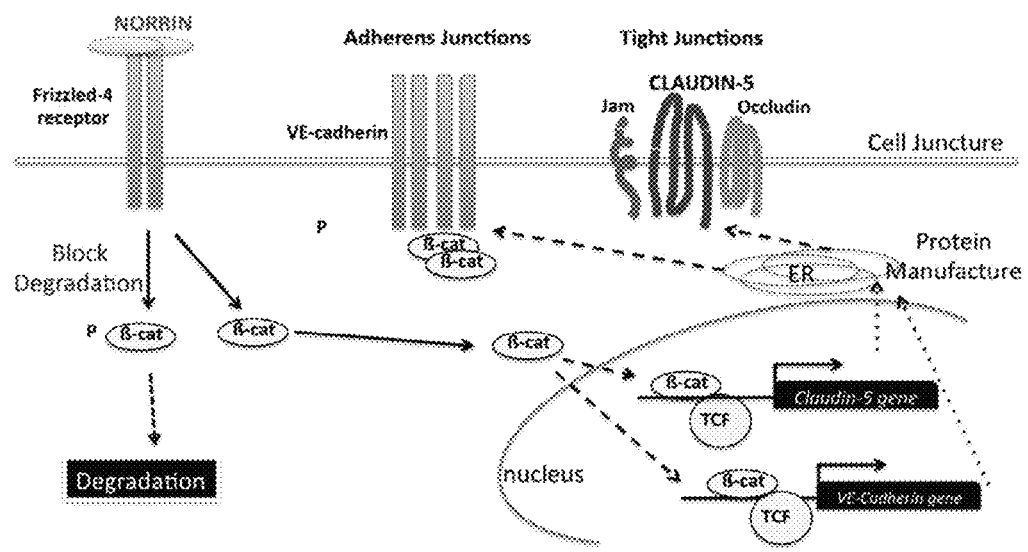
FIG. 2 is a schematic of a possible pathway for the effectiveness of the present invention to induce cellular expression of VE-cadherin and claudin-5.

Without intending to be bound to a particular theory of operation, the binding of norrin protein to a frizzled-4 receptor of a retinal epithelial cell limits degradation of beta-catetin, that then accumulates and localizes to the epithelial cell nucleus and subsequently induce a cellular response via gene transduction alongside the TCF/LEF (T-cell factor/lymphoid enhancing factor). Claudin-5 and VE-cadherin genes are then transcribed and the corresponding proteins manufactured via the endoplasmic reticulum. The resulting proteins repair a compromised cell juncture. This is shown schematically in FIG. 2. The claudin-5 and VE-cadherin proteins are also subject to harvest or usage in experimental studies in certain embodiments of the invention.

The following definitions are used herein with respect to the understanding of the present invention.

"Administering" is defined herein as a means of providing norrin protein or a composition containing norrin to a subject retina. Such an administration can be by any route including, without limitation, oral, transdermal (e.g. oral mucosa), by injection (e.g., subcutaneous, intravenous, parenterally, intraperitoneally, intraocular), by inhalation (e.g., oral or nasal), or topical (e.g., eyedrops, cream, etc.). Pharmaceutical preparations are, of course, given by forms suitable for each administration route.

By "alteration" is meant a change (increase or decrease) in the expression levels or activity of a gene or polypeptide as detected by standard art known methods such as those described herein. As used herein, an alteration includes at least a 10% change in expression levels, preferably a 25% change, more preferably a 40% change, and most preferably a 50% or greater change in expression levels.

By "analog" is meant a molecule that is not identical, but has analogous functional or structural features to norrin protein. For example, a polypeptide analog retains the biological activity of a corresponding naturally-occurring norrin, while having certain biochemical modifications that enhance the analog's function relative to a naturally occurring polypeptide. Such biochemical modifications could increase the analog's protease resistance, solubility, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "control" is meant a standard or reference status.

"Detect" refers to identifying the presence, absence or amount of the analyte to be detected.

By "detectable label" is meant a composition that when linked to a molecule of interest renders the latter detectable, via spectroscopic, photochemical, biochemical, ochemica or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "fragment" is meant a portion of norrin. This portion contains, preferably, at least 40%, 50%, 60%, 70%, 80%, or 90% of the entire length of the 133 amino acid residues of the native human norrin polypeptide. A fragment may contain 40, 50, 60, 70, 80, 90, 100, 110, 120, 130 or even the complete 133 amino acids.

By "truncate" is meant to include a fragment of norrin that has a polypeptide terminus cleavage of the norrin protein of up 40 amino acid residues.

By an "isolated polypeptide" is meant a polypeptide analog of main that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

Norrin is meant to define a polypeptide or fragment thereof having at least about 85% amino acid identity to NCBI Accession No. NP_000257.1, as shown below, and having the ability to bind the frizzled-4 receptor of retinal epithelial cells.

```
gi|4557789|ref|NP_000257.1| norrin precursor
[Homo sapiens]
                                         (SEQ ID NO. 1)
MRKHVLAASFSMLSLLVIMGDTDSKTDSSFIMDSDPRRCMRHHYVDSISH

PLYKCSSKMVLLARCEGHCSQASRSEPLVSFSTVLKQPFRSSCHCCRPQT

SKLKALRLRCSGGMRLTATYRYILSCHCEECNS
```

As used herein, "obtaining" as in "obtaining an agent" includes synthesizing, purchasing, or otherwise acquiring the agent.

The term "patient" or "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the terms "treat," "treated," "treating," "treatment," and the like refer to reducing or ameliorating a disorder and/or symptoms associated therewith BRB compromise.

Typically a therapeutically effective dosage should produce a serum concentration of compound of from about 0.1 ng/ml to about 50-100 µg/ml.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Norrin is a 133 amino acid long protein that is secreted into the extracellular space. Two primary domains define the general norrin protein structure: a signal peptide directs localization of the molecule; and a cysteine-knot motif provides the tertiary confirmation required for frizzled-4 receptor binding. (Meitinger, T, et al, Nat Genet, 1993; 5:376-380; Berger, W, et al. Hum Mol Genet, 1996; 5:51-59). Truncates and fragments of norrin that retain the ability to bind frizzled-4 receptor are operative herein. In some inventive embodiments a truncate or fragment of norrin retains the cysteine-knot motif.

The importance of the cysteine knot-motif is highlighted by computer modeling that demonstrates the requirement of disulfide bonds between the cysteine residues in forming the structural confirmation of norrin. However, mutations in regions other than the cysteine knot-motif produce incomplete protein folding and result in familial exudative vitreoretinopathy (FEVR) and related vitreoretinopathies.

In certain inventive embodiments a −24 residue N-terminus truncate of norrin, with the following amino acid sequence:

```
                                              (SEQ ID NO. 2)
KTDSSFIMDSDPRRCMRHHYVDSISHPLYKCSSKMVLLARCEGHCSQASR

SEPLVSFSTVLKQPFRSSCHCCRPQTSKLKALRLRCSGGMRLTATYRYIL

SCHCEECNS (Accession # Q00604)
```

It has been found that some fragments and truncations such as SEQ ID NO: 2 have improved solubility compared to norrin.

The invention further embraces variants and equivalents which are substantially homologous to norrin and still retain the ability to selectively hind the frizzled-4 receptor. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid.

Figure 6:
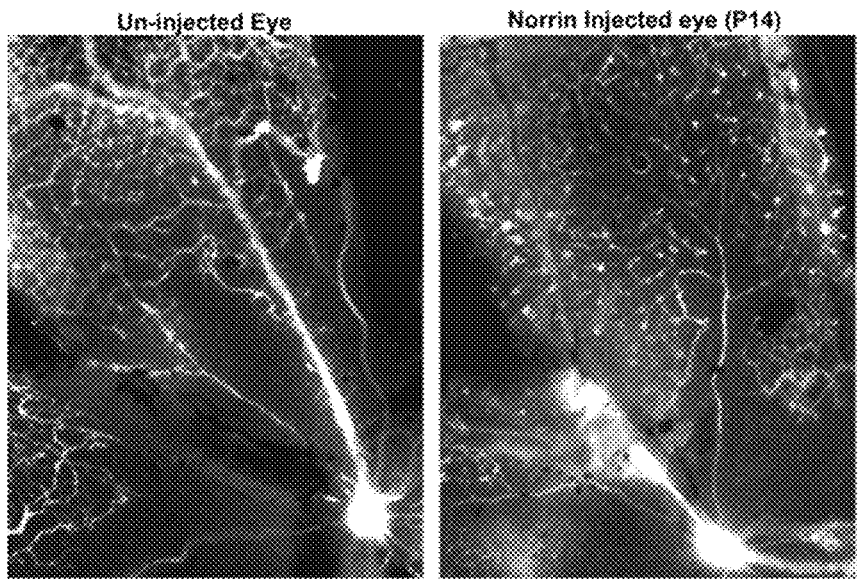
FIG. 6 are retinal micrographs depicting Evans Blue leakage in eyes of an oxygen induced retinopathy (OIR) model of a mouse, with an uninjected eye (left panel) and an eye injected with norrin (right panel), the images taken 3 days after norrin injection, where bright (white) is indicative of vascular leakage and the injected eye shows preservation of the capillary network.

The norrin of the present invention can be recombinant norrin, natural norrin, or synthetic norrin retaining frizzled-4 binding properties. It will be recognized in the art that some amino acid sequences of the invention can be varied without significant effect of the structure or function of the protein. Thus, the invention further includes variations of the norrin which show substantial activity; such mutants include deletions, insertions, inversions, repeats, and type substitutions. Norrin mutants operable herein illustratively include amino acid substitutions relative to SEQ ID NO: 1 of R64E: MRKHVLAASFSMLSLLVIMGDTDSKTDSSFIMDSDPRRCMRHHYVDSISHPLYKCSSKM VLLAECEGHCSOASRSEPLVSFSTVLKOPFRSSCHCCRPOTSKLKALRLRCSGGMRLTAT YRYILSCHCEECNS (SEQ ID NO. 3). Optionally the biologically active peptide is a multiple mutant relative to SEQ ID NO: 1: T27A: MRKHVLAASFSMLSLLVIMGDTDSKADSSFIMDSDPRRCMRHHYVDSISHPLYKCSSKM VLLARCEGHCSOASRSEPLVSFSTVLKOPFRSSCHCCRPOTSKLKALRLRCSGG MRLTAT YRYILSCHCEECNS (SEQ ID NO. 4), S28A: MRKHVLAASFSMLSLLVIMGDTDSKTDASFIMDSDPRRCMRHHYVDSISHPLYKCSSKM VLLARCEGHCSOASRSEPLVSFSTVLKOPFRSSCHCCRPOTSKLKALRLRCSGGMRLTAT YRYILSCHCEECNS (SEQ ID NO. 5), S29A MRKHVLAASFSMLSLLVIMGDTDSKTDSAFIMDSDPRRCMRHHYVDSISHPLYKCSSKM VLLARCEGHCSQASRSEPLVSFSTVLKQPFRSSCHCCRPQTSKLKALRLRCSGGMRLTAT YRYILSCHCEECNS (SEQ ID NO. 6); P36A: MRKHVLAASFSMLSLLVIMGDTDSKTDSSFIMDSDARRCMRHHYV DSISHPLYKCSSKM VLLARCEGHCSOASRSEPLVSFSTVLKOPFRSSCHCCRPOTSKLKALRLRCSGGMRLTAT YRYILSCHCEECNS (SEQ ID NO. 7), R37A: MRKHVLAASFSMLSLLVIMGDTDSKTDSSFIMDSDPARCMRHHYVDSISHPLYKCSSKM VLLARCEGHCSOASRSEPLVSFSTVLKOPFRSSCHCCRPOTSKLKALRLRCSGGMRLTAT YRYILSCHCEECNS (SEQ ID NO. 8), R38A: MRKHVLAASFSMLSLLVIMGDTDSKTDSSFIMDSDPRACMRHHHYVDSISHPLYKCSSKM VLLARCEGHCSOASRSEPLVSFSTVLKOPFRSSCHCCRPOTSKLKALRLRCSGGMRLTAT YRYILSCHCEECNS (SEQ ID NO. 9); Y120A: MRKHVLAASFSMLSLLVIMGDTDSKTDSSFIMDSDPRRCMRHHYV DSISHPLYKCSSKM VLLARCEGHCSOASRSEPLVSFSTVLKOPFRSSCHCCRPOTSKLKALRLRCSGGMRLTAT ARYILSCHCEECNS (SEQ ID NO. 10), R121A: MRKHVLAASFSMLSLLVIMGDTDSKTDSSFIMDSDPRRCMRHHYVDSISHPLYKCSSKM VLLARCEGHCSOASRSEPLVSFSTVLKOPFRSSCHCCRPOTSKLKALRLRCSGGMRLTAT YAYILSCHCEECNS (SEQ ID NO. 11), Y122A: MRKHVLAASFSMLSLLVIMGDTDSKTDSSFIMDSDPRRCMRHHYVDSISHPLYKCSSKM VLLARCEGHCSOASRSEPLVSFSTVLKOPFRSSCHCCRPOTSKLKALRLRCSGGMRLTAT YRAILSCHCEECNS (SEQ ID NO. 12); or H127A: MRKHVLAASFSMLSLLVIMGDTDSKTDSSFIMDSDPRRCMRHHYV DSISHPLYKCSSKM VLLARCEGHCSQASRSEPLVSFSTVLKQPFRSSCHCCRPQTSKLKALRLRCSGGMRLTAT YRYILSCACEECNS (SEQ ID NO. 13), E129A: MRKHVLAASFSMLSLLVIMGDTDSKTDSSFIMDSDPRRCMRHHYVDSISHPLYKCSSKM VLLARCEGHCSQASRSEPLVSFSTVLKQPFRSSCHCCRPQTSKLKALRLRCSGGMRLTAT YRYILSCHCAECNS (SEQ ID NO. 14), E130A: MRKHVLAASFSMLSLLVIMGDTDSKTDSSFIMDSDPRRCMRHHYVDSISHPLYKCSSKM VLLARCEGHCSOASRSEPLVSFSTVLKQPFRSSCHCCRPOTSKLKALRLRCSGGMRLTAT YRYILSCHCEACNS (SEQ ID NO. 15); or combinations thereof. Any amino acid mutated in a multiple mutation is operable as a single mutation. Other sequence mutations operative herein are illustrated in FIG. 6A of Smallwood, P M, et al, J Biol Chem, 2007: 282:4057-4068 or Ke, J et al. Gene & Dev. 2013: 27: 2305-2319. These mutations include K86E: MRKHVLAASFSMLSLLVIMGDTDSKTDSSFIMDSDPRRCMRHHYVDSISHPLYKCSSKM VLLARCEGHCSOASRSEPLVSFSTVLEQPFRSSCHCCRPOTSKLKALRLRCSGGMRLTAT YRYILSCHCEECNS (SEQ ID NO. 16), R90E: MRKHVLAASFSMLSLLVIMGDTDSKTDSSFIMDSDPRRCMRHHYVDSISHPLYKCSSKM VLLARCEGHCSOASRSEPLVSFSTVLKOPFESSCHCCRPOTSKLKALRLRCSGGMRLTAT YRYILSCHCEECNS (SEQ ID NO. 17), R97E: MRKHVLAASFSMLSLLVIMGDTDSKTDSSFIMDSDPRRCMRHHYVDSISHPLYKCSSKM VLLARCEGHCSASRSEPLVSFSTVLKOPFRSSCHCCEPOTSKLKALRLRCSG GMRLTAT YRYILSCHCEECNS (SEQ ID NO. 18), K102E: MRKHVLAASFSMLSLLVIMGDTDSKTDSSFIMDSDPRRCMRHHYVDSISHPLYKCSSKM VLLARCEGHCSQASRSEPLVSFSTVLKQPFRSSCHCCRPQTSELKALRLRCSGGMRLTAT YRYILSCHCEECNS (SEQ ID NO. 19), K104E: MRKHVLAASFSMLSLLVIMGDTDSKTDSSFIMDSDPRRCMRHHYVDSISHPLYKCSSKM VLLARCEGHCSQASRSEPLVSFSTVLKQPFRSSCHCCRPQTSKLEALRLRCSGGMRLTAT YRYILSCH- CEECNS (SEQ ID NO. 20), and R115E: MRKHVLAASF-SMLSLLVIMGDTDSKTDSSFIMDSDPRRCMRHHYV DSISHPLYKCSSKM VLLARCEGHCSOASRSEPLVSF-STVLKOPFRSSCHCCRPOTSKLKALRLRC-SGGMELTAT YRYILSCHCEECNS (SEQ ID NO. 21). It is appreciated that other mutations at different amino acid sites are similarly operable. It is further appreciated that mutation of the conserved amino acid at any particular site is preferably mutated to glycine or alanine. It is further appreciated that mutation to any neutrally charged, charged, hydrophobic, hydrophilic, synthetic, non-natural, non-human, or other amino acid is similarly operable.

Modifications and changes are optionally made in the structure (primary, secondary, or tertiary) of the Norrin protein which are encompassed within the inventive compound that may or may not result in a molecule having similar characteristics to the exemplary polypeptides disclosed herein. It is appreciated that changes in conserved amino acid bases are most likely to impact the activity of the resultant protein. However, it is further appreciated that changes in amino acids operable for receptor interaction, resistance or promotion of protein degradation, intracellular or extracellular trafficking, secretion, protein-protein interaction, post-translational modification such as glycosylation, phosphorylation, sulfation, and the like, may result in increased or decreased activity of an inventive compound while retaining some ability to alter or maintain a physiological activity. Certain amino acid substitutions for other amino acids in a sequence are known to occur without appreciable loss of activity.

In making such changes, the hydropathic index of amino acids are considered. According to the present invention, certain amino acids can be substituted for other amino acids having a similar hydropathic index and still result in a polypeptide with similar biological activity. Each amino acid is assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Without intending to be limited to a particular theory, it is believed that the relative hydropathic character of the amino acid determines the secondary structure of the resultant polypeptide, which in turn defines the interaction of the polypeptide with other molecules. It is known in the art that an amino acid can be substituted by another amino acid having a similar hydropathic index and still obtain a functionally equivalent polypeptide. In such changes, the substitution of amino acids whose hydropathic indices are within .+−.2 is preferred, those within .+−.1 are particularly preferred, and those within .+−.0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu).

The norrin and analogs can be further modified to contain additional chemical moieties not normally part of the protein. Those derivatized moieties can improve the solubility, the biological half-life, absorption of the protein, or binding affinity. The moieties can also reduce or eliminate any desirable side effects of the proteins and the like. An overview for those moieties can be found in. Remington's Pharmaceutical Sciences, 20th ed., Mack Publishing Co., Easton, Pa. (2000).

The isolated norrin described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. (Zoeller et al., Proc. Nat'l. Acad. Sci. USA 81:5662-5066 (1984) and U.S. Pat. No. 4,588,585).

According to the present invention, the Tight Junctions and Adherens Junctions of retinal epithelial cells with compromised junctions are exposed to a dosage of norrin, a truncate or fragment thereof. After norrin exposure the resulting cells have demonstrably higher levels of cellular junction claudin-5 and VE-cadherins. The present invention thus reverses the effects of cytokines including VEGF on retinal and choroidal epithelial cells. Retinal edema and retinal detachment associated with compromised retinal or choroidal epithelial cells junctions is thereby reduced.

Norrin truncate of SEQ ID NO: 2 is observed to be effective in increasing cellular junction levels of claudin-5 and VE-cadherins at concentrations of 10 to 1000 ng/ml.

The present invention is also directed to pharmaceutical compositions comprising an effective amount of norrin alone or in combination with a pharmaceutically acceptable carrier, excipient or additive. Particularly favored derivatives are those that increase the bioavailability of administered to a mammal (e.g., by allowing ocularly of choroidal administered norrin to be more readily absorbed into the blood) or which enhance delivery of the norrin to a biological compartment (e.g., the retina) relative to the native protein.

To prepare the pharmaceutical compositions according to the present invention, a therapeutically effective amount of norrin is preferably intimately admixed with a pharmaceutically acceptable carrier according to conventional pharmaceutical compounding techniques to produce a dose. A carrier may take a wide variety of forms depending on the form of preparation desired for administration, e.g., ocular, oral, topical orparenteral, including gels, creams ointments, lotions and time released implantable preparations, among numerous others.

Norrin is also administered with an adjunct therapeutic such as an anti-VEGF agent. An anti-VEGF agent opera herein illustratively includes bevacizumab ranibizumab small molecules that inhibit the tyrosine kinases stimulated by VEGF such as lapatinib, sunitinib, sorafenib, axitinib, pazopanib, or a combination thereof. A combination therapeutic provided that includes an anti-VEGF agent and a norrin. It has been surprisingly found that by simultaneously suppressing VEGF binding to a cell and stimulation of Tight Junction and Adherens Junction protein expression that the efficacy of conventional anti-VEGF agents is enhanced. By way of example, anti-VEGF agents are typically effective in approximately 75% of subject with the indication of macular edema secondary to diabetes. This effectiveness is increased by more to more than 85% with simultaneous administration of a norrin.

Solutions or suspensions used for ocular, parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Administration in the form of a liquid oral preparation uses a carrier in a form such as suspensions, elixirs and solutions, suitable carriers and additives including water, glycols, oils, alcohols, flavoring agents, preservatives, coloring agents and the like may be used. For solid oral administration, preparations are provided in a form such as powders, tablets, capsules, and for solid preparations such as suppositories, suitable carriers and additives including starches, sugar carriers, such as dextrose, mannitol, lactose and related carriers, diluents, granulating agents, lubricants, binders, or disintegrating agents. If desired, the tablets or capsules may be enteric-coated or sustained release by standard techniques. Norrin is provided in a solid dose is lyophilized form or in pelletized solution droplets.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, poly anhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

Formulations suitable for topical administration to the skin may be presented as ointments, creams, gels and pastes including the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

The parenteral preparation can be enclosed in ampoules, disposable syringes or multiple dose vials made of glass or plastic. If administered intravenously, preferred carriers include, for example, physiological saline or phosphate buffered saline (PBS).

For parenteral formulations, the carrier will usually comprise sterile water or aqueous sodium chloride solution, though other ingredients including those which aid dispersion may be included. Of course, where sterile water is to be used and maintained as sterile, the norrin and carriers must also be sterilized. Injectable suspensions may also be prepared, in which case appropriate liquid carriers, suspending agents and the like may be employed.

Formulations suitable for parenteral or ocular administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Administration of the active compound may range from continuous (intravenous drip) to several oral administrations per day (for example, Q.I.D.) and may include topical, ocular, parenteral, intramuscular, intravenous, sub-cutaneous, intrachoroidal or, transdermal (which may include a penetration enhancement agent).

Application of the subject therapeutics may be local, so as to be administered at the site of interest. Various techniques can be used for providing the subject norrin at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject norrin, the subject norrin may be painted onto the organ, or may be applied in any convenient way.

Norrin may be administered through a device suitable for the controlled and sustained release of a composition effective in obtaining a desired local or systemic physiological or pharmacological effect. The method includes positioning the sustained released drug delivery system at an area wherein release of the agent is desired and allowing the agent to pass through the device to the desired area of treatment. More specifically, the norrin is administered through an ocular device suitable for direct implantation into the vitreous of the eye. Such devices of the present invention are surprisingly found to provide sustained controlled release of various norrin to treat the eye without risk of detrimental local and systemic side effects. An object of the present ocular method of delivery is to maximize the amount of drug contained in an intraocular device while minimizing its size in order to prolong the duration of the implant. See, e.g., U.S. Pat. Nos. 5,378,475; 5,773,019; 6,001,386; 6,217,895, 6,375,972, and 6,756,058.

Other methods of delivery of norrin include: an ocular delivery system that could be applied to an intra-ocular lens to prevent inflammation or posterior capsular opacification, an ocular delivery system that could be inserted directly into the vitreous, under the retina, or onto the sclera, and wherein inserting can be achieved by injecting the system or surgically implanting the system, a sustained release drug delivery system, and a method for providing controlled and sustained administration of an agent effective in obtaining a desired local or systemic physiological or pharmacological effect comprising surgically implanting a sustained release drug delivery system at a desired location.

Examples include, but are not limited to the following: a sustained release drug delivery system comprising an inner reservoir containing norrin, an inner tube impermeable to the passage of the agent, the inner tube having first and second ends and covering at least a portion of the inner reservoir, the inner tube sized and formed of a material so that the inner tube is capable of supporting its own weight, an impermeable member positioned at the inner tube first end, the impermeable member preventing passage of the agent out of the reservoir through the inner tube first end, and a permeable member positioned at the inner tube second end, the permeable member allowing diffusion of the agent out of the reservoir through the inner tube second end. A method for administering norrin to a segment of an eye, includes implanting a sustained release device to deliver norrin to the vitreous of the eye or choroid, or an implantable, sustained release device for administering a compound of the invention to a segment of an eye or choroid; a sustained release drug delivery device includes a) a drug core containing norrin; b) at least one unitary cup essentially impermeable to the passage of the agent that surrounds and defines an internal compartment to accept the drug core, the unitary cup including an open top end with at least one recessed groove around at least some portion of the open top end of the unitary cup; c) a permeable plug which is permeable to the passage of norrin, the permeable plug is positioned at the open top end of the unitary cup wherein the groove interacts with the permeable plug holding it in position and closing the open top end, the permeable plug allowing passage of the agent out of the drug core, through the permeable plug, and out the open top end of the unitary cup. A sustained release norrin delivery device includes an inner core norrin having a desired solubility and a polymer coating layer, the polymer layer being permeable to norrin, wherein the polymer coating layer completely covers the inner core.

Norrin may be administered as microspheres. For example, norrin may be purchased from R&D Systems, Minneapolis, Minn., or cloned, expressed and purified is loaded into biodegradable microspheres substantially as described by Jiang, C, et al, Mol. Vis., 2007; 13:1783-92 using the spontaneous emulsification technique of Fu, K, et al, J. Pharm Sci., 2003; 92:1582-91. Microspheres are synthesized and loaded by dissolving 200 mg of 50:50 poly (lactide-co-glycolic acid) (PLGA) in 5 ml of 4:1 volume ratio trifluoroethanol:dichloromethane supplemented with 8 mg magnesium hydroxide to minimize protein aggregation during encapsulation, 10 µg norrin may be reconstituted in 300 µl 7 mg bovine serum albumin (BSA) and 100 mg docusate sodium (Sigma-Aldrich, St. Louis, Mo.) dissolved in 3 ml PBS. The solution may be vortexed and poured into 200 ml of 1% (w/v) polyvinyl alcohol (PVA, 88% hydrolyzed) with gentle stirring. Microspheres may be hardened by stirring for three hours, collected by centrifugation, and washed three times to remove residual PVA. If the microspheres are not to be immediately injected they are rapidly frozen in liquid nitrogen, lyophilized for 72 h, and stored in a dessicator at −20° C. Norrin containing microspheres exhibit average diameters of 8 µm as determined by a particle size. Norrin may also be administered by intravitreal injection. For example, norrin in solution, may be packaged into microspheres as described above, or expressed in cells, or in purified form in solution may be exposed to the retina by intravitreal injection substantially as described by Jiang, 2007. Intravitreal injection may be performed under general anesthesia using an ophthalmic operating microscope (Moller-Wedel GmbH, Wedel, Germany) using beveled glass micro-needles with an outer diameter of approximately 100 µm. Microsphere suspensions are prepared in PBS at 2 and 10% (w/v) and briefly vortexed immediately before injection to ensure a uniform dispersion. A 30-gauge hypodermic needle may be used to perforate the sclera 1.5 mm behind the limbus. Five microliters of test sample is optionally injected by way of this passage into the vitreous using a 50 µl Hamilton Syringe (Hamilton Co, Reno, Nev.). To ensure adequate delivery and prevent shock the needle is held in place for one min after the injection is completed and subsequently withdrawn slowly. In addition, paracentesis may be simultaneously performed to relieve pressure and thereby prevent reflux.

Norrin may also be administered by delivery to the retina by a controlled release delivery system. An implantable controlled release delivery system is described in U.S. Patent Application Publication 2005/0281861 and is packaged into such as system at 100 µg per final formulated capsule. For example, a norrin containing drug delivery systems may be placed in the eye using forceps or a trocar after making a 2-3 mm incision in the sclera. Alternatively, no incision may be made and the system placed in an eye by inserting a trocar or other delivery device directly through the eye. The removal of the device after the placement of the system in the eye can result in a self-sealing opening. One example of a device that is used to insert the implants into an eye is disclosed in U.S. Patent Application Publication No. 2004/0054374 which is incorporated herein by reference. The location of the system may influence the concentration gradients of therapeutic component or drug surrounding the element, and thus influence the release rates (e.g., an element placed closer to the edge of the vitreous may result in a slower release rate). Thus, it is preferred if the system is placed near the retinal surface or in the posterior portion of the vitreous.

Preferred unit dosage formulations are those containing a daily dose or unit, daily sub-dose, as hereinabove recited, or an appropriate fraction thereof, of the administered ingredient.

The dosage regimen for norrin invention is based on a variety of factors, including the degree of BRB leakage, the route of administration, ocular volume, macular separation volume, and the particular norrin employed. Thus, the dosage regimen may vary widely, but can be determined routinely using standard methods.

In certain embodiments, norrin is administered once daily; in other embodiments, norrin is administered twice daily; in yet other embodiments, norrin is administered once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

Pharmaceutically acceptable carriers, excipients, or diluents illustratively include saline, buffered saline, dextrose, water, glycerol, ethanol, sterile isotonic aqueous buffer, and combinations thereof.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices.

Materials for use in the preparation of microspheres and/or microcapsules include biodegradable/bioerodible polymers such as PLGA, polyglactin, poly-(is butyl cyanoacrylate), poly(2-hydroxyethyl-L-glutamine) and poly(lactic acid).

Biocompatible carriers which can be used when formulating a controlled release parenteral formulation include carbohydrates such as dextrans, proteins such as albumin, lipoproteins or antibodies.

Materials for use in implants can be non-biodegradable, e.g., polydimethylsiloxane, or biodegradable such as, e.g., poly(caprolactone), polylactic acid), poly(glycolic acid) or poly(ortho esters).

Examples of preservatives include, but are not limited to, parabens, such as methyl or propyl p-hydroxybenzoate and benzalkonium chloride.

Injectable depot forms are made by forming microencapsule matrices of compound(s) of the invention in biodegradable polymers such as polylactide-polyglycolide. Depending on the ratio of compound to polymer, and the nature of the particular polymer employed, the rate of compound release can be controlled. Examples of other biodegradable polymers include poly(orthoesters) and poly(anhydrides). Depot injectable formulations are also prepared by entrapping the drug in liposomes or microemulsions which are compatible with body tissue.

Any of the above-described controlled release, extended release, and sustained release compositions can be formulated to release the active ingredient in about 30 minutes to about 1 week, in about 30 minutes to about 72 hours, in about 30 minutes to 24 hours, in about 30 minutes to 12 hours, in about 30 minutes to 6 hours, in about 30 minutes to 4 hours, and in about 3 hours to 10 hours. In embodiments, an effective concentration of the active ingredient(s) is sustained in a subject for 4 hours, 6 hours, 8 hours, 10 hours, 12 hours, 16 hours, 24 hours, 48 hours, 72 hours, or more after administration of the pharmaceutical compositions to the subject.

When norrin is administered as a pharmaceutical to humans or animals, norrin can be given per se or as a pharmaceutical composition containing active ingredient in combination with a pharmaceutically acceptable carrier, excipient, or diluent.

Actual dosage levels and time course of administration of the active ingredients in the pharmaceutical compositions of the invention can be varied so as to obtain an amount of the active ingredient which is effective to achieve the desired therapeutic response for a particular patient, composition, and mode of administration, without being toxic to the patient. Generally, norrin is administered in an amount sufficient to reduce or eliminate symptoms associated with retinal edema or macular degeneration or FEVR.

Exemplary ocular dose ranges include 0.00001 mg to 250 mg per day, 0.0001 mg to 100 mg per day, 1 mg to 100 mg per day, 10 mg to 100 mg per day, 1 mg to 10 mg per day, and 0.01 mg to 10 mg per day. A preferred dose of an agent is the maximum that a patient can tolerate and not develop serious or unacceptable side effects. In certain inventive embodiments, the therapeutically effective dosage produces an ocular concentration of norrin of from about 0.1 ng/ml to about 50-100 µg/ml. In certain inventive embodiments, 50 nM to 1 µM of an agent is administered to a subject eye. In related embodiments, about 50-100 nM, 50-250 nM, 100-500 nM, 250-500 nM, 250-750 nM, 500-750 nM, 500 nM to 1 µM, or 750 nM to 1 µM of an norrin is administered to a subject eye.

Determination of an effective amount is well within the capability of those skilled in the art, especially in light of the detailed disclosure provided herein. Generally, an efficacious or effective amount of a norrin is determined by first administering a low dose of the agent(s) and then incrementally increasing the administered dose or dosages until a desired effect (e.g., reduce or eliminate symptoms associated with retinal edema) is observed in the treated subject, with minimal or acceptable toxic side effects. Applicable methods for determining an appropriate dose and dosing schedule for administration of a pharmaceutical composition of the present invention are described, for example, in Goodman and Oilman's The Pharmacological Basis of Therapeutics, Goodman et al., eds., 11th Edition, McGraw-Hill 2005, and Remington: The Science and Practice of Pharmacy, 20th and 21st Editions, Gennaro and University of the Sciences in Philadelphia, Eds., Lippencott Williams & Wilkins (2003 and 2005), each of which is hereby incorporated by reference.

The following are in vitro & in vivo examples of how norrin can overcome the endothelial cell depletion of cell-to-cell adhesion molecules and re-stabilize vessels which are for purposes of illustration, and are not intended to limit the scope of the present invention.

In Vitro Assays

Example 1: Immunostain of VE-Cadherin In Cells—VEGF Challenge

Human retinal microvascular endothelial cells (HRMECs) were cultured in DMEM supplemented with 10% (v/v) heat-inactivated FBS (Nichirei Biosciences Inc., Tokyo, Japan), 100 U/mL penicillin, 100 µg/mL streptomycin (Life Technologies Gibco, France. The cell cultures were incubated on collagen-coated tissue culture plates Transwell® (Corning, New York, N.Y.) in a humidified atmosphere of 5% CO, at 37° C.

HRMECs were cultured for 14 to 21 d on a Lab-Tek chamber plate (Corning). $H_2O_2$ (500 µmol/L) was administered to the basolateral side of the Transwell®. To some plates nothing was added (Control), or VEGF (100 ng/mL) or norrin truncate (SEQ ID NO: 2) (250 ng/ml) or both VEGF and norrin (100 ng/ml and 250 ng/ml, respectively) was added to the apical medium 30 min prior to $H_2O_2$ treatment. After 6 h of incubation, the cells were washed twice with cold PBS and fixed with cold acetone (Wako Pure Chemical Industries, Osaka, Japan) for 10 min. The cells were then removed from the Transwell® and mounted on slides. Next, the cells were incubated with mouse anti-human VE-cadherin at 4° C. overnight. After washing with PBS, the cells were incubated with dye-conjugated secondary antibody specific to the anti-human VE-cadherin antibody then subsequently washed in PBS. The immunofluorescence was examined and imaged using fluorescence microscopy.

Figure 3:
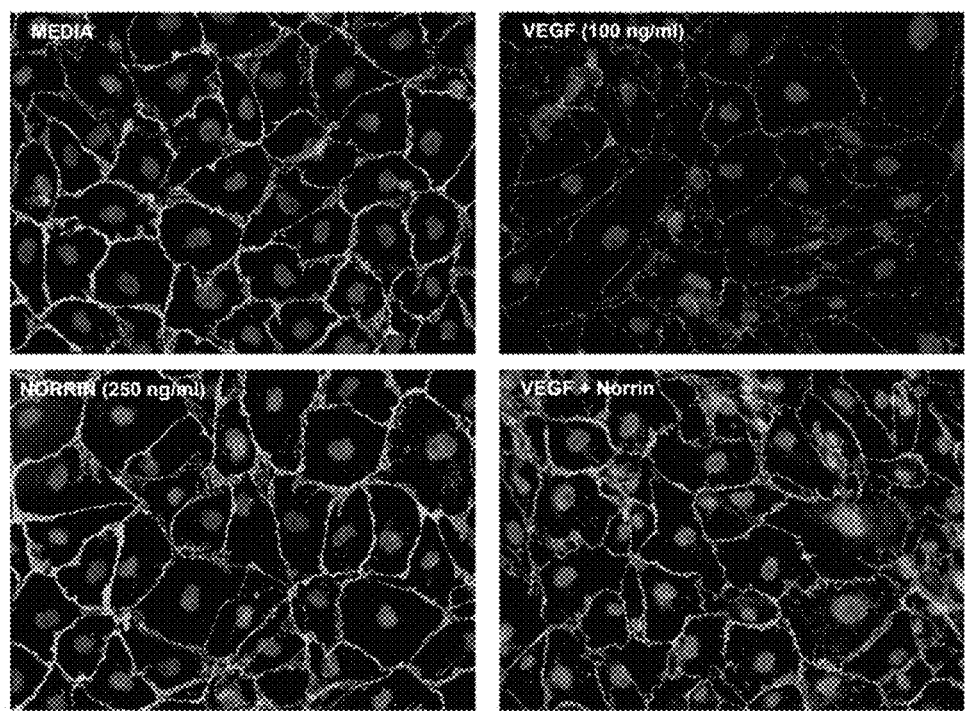
FIG. 3 are 20× magnification fluorescence micrographs of human retinal microvascular endothelial cells (HRMECs) immunostained (green at boundaries around cells) for VE-cadherin after 24 hours in media alone (upper left panel), after exposure to: VEGF (100 ng/ml of media) (upper right panel), norrin (250 ng/ml of media) (lower left panel), and both VEGF (100 ng/ml of media) and norrin (250 ng/ml of media) (lower right panel)

Under control conditions, claudin-5 are localized to cell-cell boundaries of these cells as shown in the upper left panel of FIG. 3. After addition of VEGF (upper right panel, FIG. 3) one can see a reduction in cell-cell adhesion molecules as well as a loss in the cobblestone morphology. However with the combination of VEGF and norrin (lower right panel, FIG. 3) the junction proteins and morphology were restored. The effect of norrin alone is noted (lower left panel, FIG. 3).

Example 2: Immunostain of Claudin-5 In Cells—VEGF Challenge

The process of Example 1 was repeated with mouse anti-human claudin-5 antibody at 4° C. overnight instead of anti-human VE-cadherin. After washing with PBS, the cells were incubated with dye-conjugated secondary antibody specific to the anti-human claudin 5 antibody then subsequently washed in PBS prior to being imaged using fluorescence microscopy.

Figure 4:
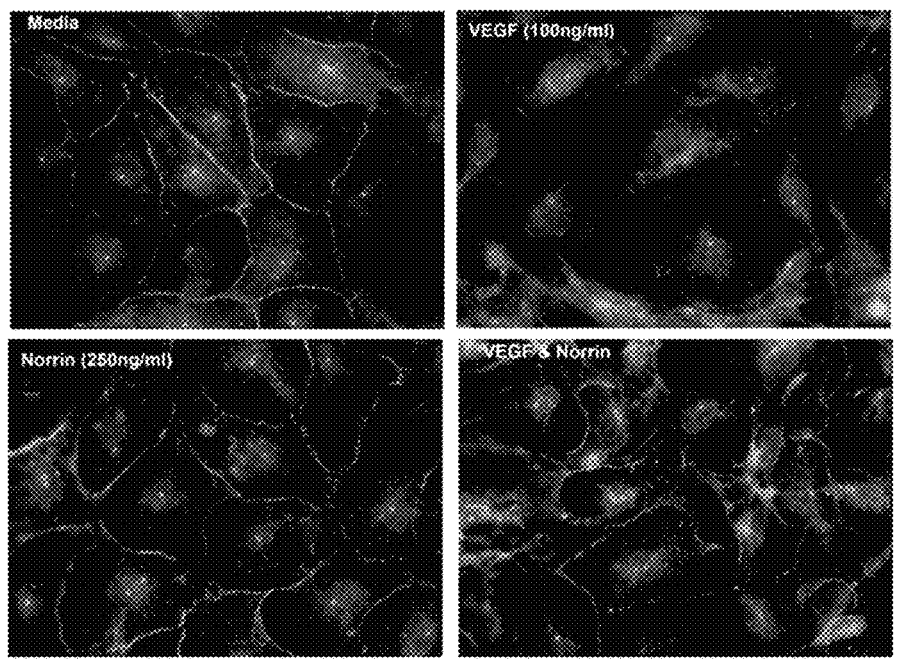
FIG. 4 are 40× magnification fluorescence micrographs of HRMECs immunostained (green at boundaries around cells) for claudin-5 after 24 hours in media alone (upper left panel), after exposure to: VEGF (100 ng/ml of media) (upper right panel), norrin (250 ng/ml of media) (lower left panel), and both VEGF (100 ng/ml of media) and norrin (250 ng/ml of media) (lower right panel)

Under control conditions, claudin-5 are localized to cell-cell boundaries of these cells as shown in the upper left panel of FIG. 4. After addition VEGF (upper right panel, FIG. 4) one can see a reduction in cell-cell adhesion molecules as well as a loss in the cobblestone morphology. However with the combination of VEGF and norrin (lower right panel, FIG. 4) the junction proteins and morphology were restored. The effect of norrin alone is noted (lower left panel, FIG. 4).

Example 3: Claudin-5 mRNA Expression in Cells—VEGF Challenge

Figure 5:
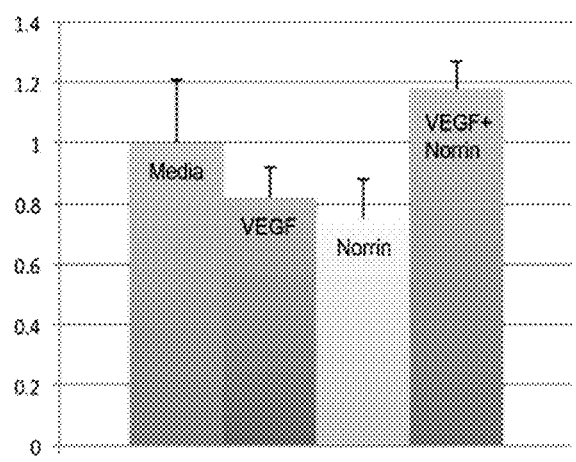
FIG. 5 is a normalized bar graph of mRNA expression of claudin-5 in a monolayer of HRMECs 24 hours after no addition, VEGF, norrin, or the combination of VEGF and norrin, showing that norrin restores claudin-5 expression.

The process of Example 4 is repeated with the replacement of TGF-beta with VEGF as the challenge agent. The amount of claudin-5 mRNA detected is shown in FIG. 5 normalized to the media only control. Norrin is observed to increase claudin-5 expression levels beyond that of the media control.

Example 4: In Vivo Assays of Vessel Leakage & Claudin-5 Stain in OIR MICE

The mouse Oxygen Induced Retinopathy Model (OIR) is used to create ischemic retina so the changes in vascular morphology and function can be assessed. Raising mice in a high oxygen environment creates areas of avascular retina. Once returned to normal oxygen environment, vessels become leaky and grow in an unregulated fashion. The amount of leakage can be visualized by systemically injecting a fluorescent dye (Evans Blue or fluoroscein) and then viewing the retina under a microscope. In OIR mice, Evans blue dye can be seen leaking from retinal vessels and claudin-5 is disrupted (left panel of FIG. 6). However, in OIR eyes injected with norrin after the OIR induction of avascular retina, Evans blue dye is confined to vessels (right panel of FIG. 6). Images were taken 4 days after norrin injection in right eye.

As a person skilled in the art will recognize from the previous detailed description and from the figures and claims, modifications and changes can be made to the preferred embodiments of the invention without departing from the scope of this invention defined in the following claims.

The invention claimed is:

1. A method of treating edema in a retina of a living subject by tightening inter-cellular junctions in retinal vessel cells or choroidal vessel cells defining a tissue comprising:
administering by intraocular injection or solution droplets application to an eye containing the retinal vessel cells or the choroidal vessel cells an effective amount of an N-terminus norrin truncate that has a polypeptide N-terminus cleavage relative to a native norrin protein of up 40 amino acid residues retaining a cysteine-knot motif of the native norrin and capable of binding to the retinal vessel cells or the choroidal vessel cells, or a norrin mutant having at least 85% amino acid identity to SEQ ID NO. 1 and retaining a cysteine-knot motif of the native norrin and capable of binding to the retinal vessel cells or the choroidal vessel cells; and
allowing sufficient time for said N-terminus norrin truncate or said norrin mutant to selectively up-regulate gene expression of VE-cadherin and claudin-5 in the retinal vessel cells or the choroidal vessel cells to tighten the inter-cellular junctions of the tissue for prevention of vascular leakage or repair of the vascular leakage to treat the edema in the retina.

2. The method of claim 1, wherein said subject is human.

3. The method of claim 1, wherein said subject is one of: cow, horse, sheep, pig, goat, chicken, cat, dog, mouse, guinea pig, hamster, rabbit, or rat.

4. The method of claim 1, further comprising diagnosing retina edema associated with fluid leakage from a retinal vessel defined by retinal vessel cells prior to the exposing step.

5. The method of claim 1, wherein said N-terminus norrin truncate consists of: a polypeptide of SEQ ID. NO. 2.

6. The method of claim 1, wherein said N-terminus norrin truncate or norrin mutant is selected from the group consisting of SEQ ID. NO. 3, 5, 6, 7, 8, 9, 10, 11, 14, and 16.

7. The method of claim 1, wherein said N-terminus norrin truncate or norrin mutant is selected from the group consisting of SEQ ID. NO. 12, 13, 14, 15, 17, 18, 19, 20, and 21.

8. The method of claim 1, wherein said N-terminus norrin truncate or said norrin mutant is recombinant.

9. The method of claim 1, further comprising bringing a dye into contact with the retinal vessel cells after the allowing sufficient time for said norrin to selectively up-regulate gene expression of VE-cadherin or claudin-5 to measure a tightness of the inter-cellular junctions.

10. The method of claim 9, wherein said dye is an immunostain for claudin-5 or VE-cadherin.

11. The method of claim 9, wherein said dye is Evans Blue dye or fluoroscein.

12. The method of claim 1 wherein the tissue is experiencing edema prior to the administering step.

13. A method of treating edema in a retina of a living subject by tightening inter-cellular junctions in retinal vessel cells or choroidal vessel cells defining a tissue comprising:
administering by intraocular injection or solution droplets application to an eye containing the retinal vessel cells or the choroidal vessel cells an effective amount of an N-terminus norrin truncate that has a polypeptide N-terminus cleavage relative to a native norrin protein of up 40 amino acid residues retaining a cysteine-knot motif of the native norrin and capable of binding to the retinal vessel cells or the choroidal vessel cells, or a norrin mutant having at least 85% amino acid identity to SEQ ID NO. 1 and retaining a cysteine-knot motif of the native norrin and capable of binding to the retinal vessel cells or the choroidal vessel cells;
administering in concert with said N-terminus norrin truncate or norrin mutant and by intraocular injection or solution droplets application to the eye containing the retinal vessel cells or the choroidal vessel cells an effective amount an anti-VEGF agent selected from the group consisting of: bevacizumab, ranibizumab, lapatinib, sunitinib, sorafenib, axitinib, pazopanib, or a combination thereof and
allowing sufficient time for said N-terminus norrin truncate or said norrin mutant to selectively up-regulate gene expression of VE-cadherin and claudin-5 in the retinal vessel cells or the choroidal vessel cells to tighten the inter-cellular junctions of the tissue for prevention of vascular leakage or repair of the vascular leakage to treat the edema in the retina.

\* \* \* \* \*